(12) United States Patent
Olson et al.

(10) Patent No.: US 7,642,233 B2
(45) Date of Patent: Jan. 5, 2010

(54) ENHANCING RECOMBINANT HEMOGLOBIN PRODUCTION BY CO-EXPRESSION WITH ALPHA HEMOGLOBIN STABILIZING PROTEIN

(75) Inventors: John S. Olson, Houston, TX (US); Mitchell J. Weiss, Wynnewood, PA (US)

(73) Assignees: William Marsh Rice University, Houston, TX (US); The Children's Hospital of Philadelphia, Philadelphia, PA (US)

(*) Notice: Subject to any disclaimer, the term of this patent is extended or adjusted under 35 U.S.C. 154(b) by 0 days.

(21) Appl. No.: 11/685,986

(22) Filed: Mar. 14, 2007

(65) Prior Publication Data

US 2007/0154993 A1 Jul. 5, 2007

Related U.S. Application Data

(63) Continuation of application No. PCT/US2005/033028, filed on Sep. 15, 2005.

(60) Provisional application No. 60/610,108, filed on Sep. 15, 2004, provisional application No. 60/610,109, filed on Sep. 15, 2004, provisional application No. 60/610,110, filed on Sep. 15, 2004.

(51) Int. Cl.
*C07K 14/00* (2006.01)

(52) U.S. Cl. .......................... 514/6; 530/385

(58) Field of Classification Search ........................ None
See application file for complete search history.

(56) References Cited

U.S. PATENT DOCUMENTS

| | | | |
|---|---|---|---|
| 5,028,588 A | 7/1991 | Hoffman et al. | 514/6 |
| 5,239,061 A | 8/1993 | Fronticelli et al. | 530/385 |
| 5,240,831 A | 8/1993 | Barnes | 435/69.1 |
| 5,286,638 A | 2/1994 | Tanaka et al. | 435/192 |
| 5,827,693 A | 10/1998 | De Angelo et al. | 435/69.6 |
| 6,022,849 A | 2/2000 | Olson et al. | 514/6 |
| 6,114,505 A | 9/2000 | Olson et al. | 530/385 |
| 6,172,039 B1 | 1/2001 | De Angelo et al. | 514/6 |
| 6,204,009 B1 | 3/2001 | Olson et al. | 435/69.1 |
| 6,455,676 B1 | 9/2002 | Weichert et al. | 530/385 |
| 7,019,406 B2 | 3/2006 | Huang et al. | 257/778 |
| 7,049,406 B2 | 5/2006 | Weickert et al. | 530/385 |
| 2005/0048479 A1 | 3/2005 | Gandhi et al. | 435/6 |
| 2007/0154993 A1 | 7/2007 | Olson et al. | 435/69.6 |
| 2007/0166792 A1 | 7/2007 | Olson et al. | 435/69.1 |

FOREIGN PATENT DOCUMENTS

WO    96/41885    12/1996

OTHER PUBLICATIONS

Thunell et al. 2000. Porphyrins, porphyrin metabolism, and porphyrias. I. Update. Scand J Clin Lab Invest. 60:509-540.*
McGovern, P. et al., (1976) J Biol Chem 251, 7871-7879.
Ip, S. H. et al., (1976) Biochemistry 15, pp. 654-660.
O'Malley, S. M. et al., (1994) J Protein Chem 13, pp. 585-590.
Wycuff, D. R. and Matthews, K. S., Generation of an AraC-araBAD Promoter-Regulated T7 Expression System (2000) Anal. Biochem. 277, pp. 67-73.
Kihm et al., An Abundant Erythroid Portien That Stabilizes Free Alpha-Hemoglobin, Nature 13, vol. 417, pp. 758-763, Jun. 2002.
Gell, D. et al., (2002) J Biol Chem 277, 40602-40609.
Luzzatto, L. et al., (2002) Nature 417, pp. 703-705.
Kong, Y. et al. (2004) J Clin. Invest.
Santiveri, C. M. et al., (2004) J Biol Chem.
Baudin-Creuza, v. et al., (2004) J Biol Chem.
dos Santos, C.O. et al., (2004) Exp Hematol 32, pp. 157-162.
Feng et al., Molecular Mechanism Of AHSP-Mediated Stabilization Of β—Hemoglobin, Cell, vol. 119, 629-640, 12 pages, Nov. 24, 2004.
Feng et al., Structure of Oxidized β—Haemoglobin Bound To AHSP Reveals a Protective Mechanism for Haem, Nature Publishing Group, vol. 435, pp. 697-701, Jun. 2, 2005.
International Search Report and Written Opinion, PCT/US05/33028, 11 pages, Oct. 3, 2006.
U.S. Appl. No. 60/610,109, filed Sep. 15, 2004, Olson et al.
U.S. Appl. No. 60/610,108, filed Sep. 15, 2004, Olson et al.
Abbasi et al. "The Primary Structure of Sperm Whale Hemoglobin (*Physeter catodon*, Cetacea)" Biol. Chem Hoppe-Seyler, vol. 367 (pp. 355-361), Apr. 1986.
Ackers "Deciphering The Molecular Code Of Hemoglobin Allostery" Dept. Of Biochemistry and Biophysics, Washington University (pp. 185-253), 1998.
Ackers "Energetics Of Subunit Assembly And Ligand Binding In Human Hemoglobin" Dept. of Biology and McCollum Pratt Institute, The Johns Hopkins University (pp. 331-346), 1980.
Adachi et al. "Assembly of γ- with α-Globin Chains to Form Human Fetal Hemoglobin in Vitro and in Vivo" J Biol Chem, vol. 275, Issue 17 (16 pages), Apr. 28, 2000.
Adachi et al. "Consequence of β16 and β112 Replacements on the Kinetics of Hemoglobin Assembly" Biochemical and Biophysical Research Communications, vol. 289 (pp. 75-79), 2001.
Adachi et al. "Significance of β16 His (G18) at α1β1 Contact Sites for αβ Assembly and Autoxidation of Hemoglobin" Biochemistry, vol. 42 (pp. 10252-10259), Apr. 16, 2003.
Andrews et al. "Bacterial iron homeostasis" FEMS Microbiology Review 27 (pp. 215-237), 2003.
Antonini, E. and Brunori M., "Hemoglobin and Myoglobin in Their Reactions with Ligands", North-Holland Publishing Company, Amsterdam, London, 1971, (pp. 110-119, 126-129).
Ascoli et al. "Preparation and Properties of Apohemoglobin and Reconstituted Hemoglobins" Methods in Enzymology, vol. 76 (pp. 72-87), 1981.

(Continued)

*Primary Examiner*—Karen Cochrane Carlson
(74) *Attorney, Agent, or Firm*—Baker Botts L.L.P.

(57) ABSTRACT

The present disclosure relates to the use of AHSP to stabilize the α subunit of rHb. AHSP may be co-expressed with the hemoglobin genes. AHSP stabilization may be used to increase the production of intact rHb in various systems, such as *E. coli*, other microorganisms, or animal erythroid cells. This intact rHb may then be used as part of a blood substitute product.

20 Claims, 2 Drawing Sheets

OTHER PUBLICATIONS

Bagg et al. "Ferric Uptake Regulation Protein Acts as a Repressor, Employing Iron (II) as a Cofactor To Bind the Operator of an Iron Transport Operon in *Escherichia coli*" Biochemistry, vol. 26 (pp. 5471-5477), 1987.

Barrick et al. "Three-State Analysis of Sperm Whale Apomyoglobin Folding" Biochemistry, vol. 32 (pp. 3790-3796), Feb. 1, 1993.

Benesch et al. "The Stability of the Heme-Globin Linkage in Some Normal, Mutant, and Chemically Modified Hemoglobins" The Journal of Biological Chemistry, vol. 265, No. 25 (pp. 14881-14885), Feb. 9, 1990.

Bunn et al. "Exchange of Heme among Hemoglobins and between Hemoglobin and Albumin" The Journal of Biological Chemistry, vol. 243, No. 3 (pp. 465-475), Jun. 19, 1967.

Bunn et al. "Electrostatic interactions in the assembly of haemoglobin" Nature 306 (pp. 498-500), Dec. 1983.

Bunn, H.F. and Forget B.G., "Hemoglobin: Molecular, Genetic and Clinical Aspects", W.B. Saunders Company, Philadelphia, 1986, (pp. 68-75).

Chu et al. "Interaction of Human Apohemoglobin with Inositol Hexaphosphate" The Journal of Biological Chemistry, vol. 254, No. 2 (pp. 371-376), Jan. 25, 1979.

Daskaleros et al. "Iron Uptake in *Plesiomonas shigelloides*: Cloning of the Genes for the Heme-Iron Uptake System" Infection and Immunity, vol. 59, No. 8 (pp. 2706-2711), Aug. 1991.

Dodson et al. "Apomyoglobin as a molecular recognition surface: expression, reconstitution and crystallization of recombinant porcine myoglobin in *Escherichia coli*" Protein Engineering vol. 2, No. 3 (pp. 233-237), 1988.

Dou et al. "Myoglobin as a model system for designing heme protein based blood substitutes" Biophysical Chemistry 98 (pp. 127-148), 2002.

Dumoulin et al. "The N-terminal Sequence Affects Distant Helix Interactions in Hemoglobin" The Journal of Biological Chemistry, vol. 273, No. 52 (pp. 35032-35038), Dec. 25, 1998.

Edelstein "Cooperative Interactions of Hemoglobin" Annu Review Biochem 44 (pp. 209-232), 1975.

Eliezer et al. "Native and Non-native Secondary Structure and Dynamics in the pH 4 Intermediate of Apomyoglobin" Biochemistry 39 (pp. 2894-2901), Jan. 7, 2000.

Eliezer et al. "Populating the equilibrium molten globule state of apomyoglobin under conditions suitable for structural characterization by NMR" Federation of European Biochemical Sciences Letter 417 (pp. 92-96), Sep. 11, 1997.

Eliezer et al. "Structural and dynamic characterization of partially folded states of apomyoglobin and implications for protein folding" Nature Structural Biology 5 (pp. 148-155), Feb. 1998.

Fronticelli et al. "Alloseric Modulation by Tertiary Structure in Mammalian Hemoglobins" The Journal of Biological Chemistry, vol. 270, No. 51 (pp. 30588-30592), Dec. 22, 1995.

Garcia et al. "Changes in Apomyoglobin Folding Pathway Caused by Mutation of the Distal Histidine Residue" Biochemistry 39 (pp. 11227-11237), 2000.

Gattoni et al. "Stability of the Heme-Globin Linkage in αβ Dimers and Isolated Chains of Human Hemoglobin" The Journal of Biological Chemistry, vol. 271, No. 17 (pp. 10130-10136). Apr. 26, 1996.

Genco et al. "Emerging strategies in microbial haem capture" Molecular Microbiology, vol. 39 (pp. 1-11), 2001.

Ghigo et al. "A New Type of Hemophore-Dependent Heme Acquisition System of *Serratia marcescens* Reconstituted in *Escherichia coli*" Journal of Bacteriology, vol. 179, No. 11 (pp. 3572-3579), Jun. 1997.

Gibson et al. "Kinetic Studies on the Reaction between Native Globin and Haem Derivatives" Biochem J 77 (pp. 328-341), 1960.

Gibson et al. "Rates of Reaction of Native Human Globin with Some Hemes" The Journal of Biological Chemistry, vol. 258, No. 4 (pp. 1384-1388), Apr. 1963.

Griggs et al. "Mechanism for Iron-Related Transcription of the *Escherichia coli cir* Gene: Metal-Dependent Binding of Fur Protein to the Promoters" Journal of Bacteriology, vol. 171, No. 2 (pp. 1048-1054), Feb. 1989.

Hargrove et al. "Stability of Myoglobin: A Model for the Folding of Heme Proteins" Biochemistry 33 (pp. 11767-11775), Jun. 14, 1994.

Hargrove et al. "The Association Rate Constant for Heme Binding to Globin is Independent of Protein Structure" Biochemistry 35 (pp. 11293-11299), 1996.

Hargrove et al. "The Stability of Holomyoglobin is Determined by Heme Affinity" Biochemistry 35 (pp. 11310-11318), 1996.

Hargrove et al. "Quaternary Structure Regulates Hemin Dissociation from Human Hemoglobin" Journal of Biololgical Chemistry vol. 272, No. 28 (pp. 17385-17389), 1997.

Henderson et al. "Characterization of the *Plesiomonas shigelloides* Genes Encoding the Heme Iron Utilization System" Journal of Bacteriology, vol. 183, No. 9 (pp. 2715-2723), May 2001.

Henderson et al. "Characterization of the *Vibrio cholerae* Outer Membrane Heme Transport Protein HutA: Sequence of the Gene, Regulation of Expression, and Homology to the Family of TonB-Dependent Proteins" Journal of Bacteriology, vol. 176, No. 11 (pp. 3269-3277), Jun. 1994.

Henderson et al. "Cloning and characterization of the *Vibrio cholerae* genes encoding the utilization of iron from haemin and haemoglobin" Molecular Microbiology, vol. 7 (pp. 461-469), 1993.

Henderson et al. "*Vibrio cholerae* Iron Transport Systems: Roles of Heme and Siderophore Iron Transport in Virulence and Identification of a Gene Associated with Multiple Iron Transport Systems" Infection and Immunity, vol. 62, No. 11 (pp. 5120-5125), Nov. 1994.

Hughson et al. "Structural Characterization of a Partly Folded Apomyoglubin Intermediate" Science vol. 249 (pp. 1544-1548), 1990.

International Preliminary Report on Patentability and Written Opinion for International Application No. PCT/US2005/032627 (5 pages), Mar. 29, 2007.

International Preliminary Report on Patentability and Written Opinion for International Application No. PCT/US2005/033027 (6 pages), Mar. 29, 2007.

International Preliminary Report on Patentability and Written Opinion for International Application No. PCT/US2005/033028 (6 pages), Mar. 29, 2007.

International Search Report and Written Opinion for International Application No. PCT/US2005/032627 (8 pages), Mar. 14, 2006.

International Search Report and Written Opinion for International Application No. PCT/US2005/033027 (9 pages), Nov. 1, 2006.

International Search Report and Written Opinion for International Application No. PCT/US2005/033028 (11 pages), Oct. 3, 2006.

Ip et al. "Kinetics of Deoxyhemoglobin Subunit Dissociation Determined by Haptoglobin Binding: Estimation of the Equilibrium Constant from Forward and Reverse Rates" Biochemistry vol. 15, No. 3 (pp. 654-660), 1976.

Ip et al. "Thermodynamic Studies on Subunit Assembly in Human Hemoglobin" The Journal of Biological Chemistry vol. 252, No. 1 (pp. 82-87), 1977.

Jennings et al. "Esterification of the Propionate Groups Promotes α / β Hemoglobin Chain Homogeneity of CN-hemin Binding" Biochemical and Biophysical Research Communications 293 (pp. 1354-1357), 2002.

Joshi, J "Role of α and β Carboxyl-terminal Residues in the Kinetics of Human Oxyhemoglobin Dimer Assembly" The Journal of Biological Chemisstry, vol. 269, No. 11 (pp. 8549-8553), 1994.

Kooyman et al. "The Physiological Basis of Diving to Depth: birds and Mammals" Annu. Rev. Physiol., vol. 60 (pp. 19-32), 1998.

Kowalczyk et al. "Dimensions in Solution of Pyridoxylated Apohemoglobin" Biochemistry 22 (pp. 4805-4809), 1983.

Létoffé et al. "Free and Hemophore-Bound Heme Acquisitions through the Outer Membrane Receptor HasR Have Different Requirements for the TonB-ExbB-ExBD Complex" Journal of Bacteriology, vol. 186, No. 13 (pp. 4067-4074), Jul. 2004.

Light et al. "The Effects of Lipid Composition on the Rate and Extent of Heme Binding to Membranes" The Journal of Biological Chemistry, vol. 265, No. 26 (pp. 15632-15637), 1990.

Light et al. "Transmembrane Movement of Heme" The Journal of Biological Chemistry, vol. 265, No. 26 (pp. 15623-15631), 1990.

Litwin et al. "Role of Iron in Regulation of Virulence Genes" Clinical Microbiology Reviews, vol. 6, No. 2 (pp. 137-149), Apr. 1993.

Lloyd et al. "Formation of Sulphmyoglobin During Expression of Horse Heart Myoglobin in *Escherichia coli*" Federation of European Biochemical Societies Letters 340 (pp. 281-286), 1994.

Looker et al. "Expression of Recombinant Human Hemoglobin in*Escherichia coli*" Methods in Enzymology, vol. 231 (pp. 364-374), 1994.

McDonald et al. "Structural, Functional, and Subunit Assembly Properties of Hemoglobin Attleboro [α138 (H21) Ser → Pro], a Variant Possessing a Site Mutation at a Critical C-Terminal Residue" Biochemistry 29 (pp. 173-178), 1990.

McDonald et al. "The Kinetics of Assembly of Normal and Variant Human Oxyhemoglobins" The Journal of Biological Chemistry, vol. 262, No. 13 (pp. 5951-5956), 1987.

McDonald et al. "Subunit Assembly of Normal and Variant Human Hemoglobins" the Red Cell: Sixth Ann Arbor Conference 1984 (pp. 2-11).

McGovern et al. "Aggregation of Deoxyhemoglobin Subunits" The Journal of Biological Chemistry, vol. 251 (pp. 7871-7879).

Mills et al. "Genetics and Regulation of Heme Iron Transport in *Shigella dysenteriae* and Detection of an Analogous System in *Escherichia coli* O157:H7" Journal of Bacteriology, vol. 177, No. 11 (pp. 3004-3009) Jun. 1995.

Moulton et al. "Kinetics of Human Apohemoglobin Dimer Dissociation" Biochemical and Biophysical Research Communications, vol. 199, No. 3 (pp. 1278-1283), 1994.

Mourino et al. "Characterization of Heme Uptake Cluster Genes in the Fish Pathogen Vibrio anguillarum" J Bacteriol. vol. 186, No. 18 (1 page), Sep. 2004.

Mrabet et al. "Dissociation of Dimers of Human Hemoglobins A and F into Monomers" The Journal of Biological Chemictry, vol. 261, No. 3 (pp. 1111-1115), 1984.

Mrabet et al. "Electrostatic Attraction Governs the Dimer Assembly of Human Hemoglobin" The Journal of Biological Chemistry, vol. 261, No. 11 (pp. 5222-5228), 1986.

Musto et al. "Folding of *Aplysia limacina* Apomyoglobin Involves an Intermediate in Common with Other Evolutionarily Distant Globins" Biochemistry 43 (pp. 230-236), 2004.

Nishimura et al. "Role of the B Helix in Early Folding Events in Apomyoglobin: Evidence from Site-directed Mutagenesis for Native-like Long Range Interactions" J Mol Biol 334 (pp. 293-307), 2003.

Nishimura et al. "Conservation of Folding Pathways in Evolutionarily Distant Globin Sequences" Nature Structure Biology, vol. 7, No. 8 (pp. 679-686), 2000.

Olson et al. "Protein Engineering Strategies For Designing More Stable Hemoglobin-Based Blood Substitutes" Artificial Cells, Blood Substitutes, and Immobilization Biotechnology 25 (pp. 227-241), 1997.

Olson et al. "No Scavenging and the Hypertensive Effect of Hemoglobin-based Blood Substitutes" Free Radical Biology & Medicine, vol. 36, No. 6 (pp. 685-697), 2004.

O'Malley et al. "Monitoring the Effect of Subunit Assembly on the Structural Flexibility of Human Alpha Apohemoglobin by Steady-State Fluorescence" The Journal of Protein Chemistry, vol. 13, No. 6 (pp. 561-567), 1994.

Oton et al. "Fluorescence Studies of Internal Rotation in Apohemoglobin α-Chains" Archives of Biochemistry Biophysics, vol. 228, No. 2 (pp. 519-524), Feb. 1, 1984.

Paquelin et al. "Characterization of HasB, a *Serratia marcescens* TonB-like protein specifically involved in the haemophore -dependent haem acquisition system" Molecular Microbiology, vol. 42, No. 4 (pp. 995-1005), 2001.

Perutz. "Mechanisms Regulating the Reactions of Human Hemoglobin with Oxygen and Carbon Monoxide" Annual Review of Physiology 52 (pp. 1-25), 1990.

Perutz "Stereochemistry of Cooperative Effects in Haemoglobin" Nature, vol. 228 (pp. 726-739), Nov. 21, 1970.

Pohl et al. "Architecture of a protein central to iron homeostasis: crystal structure and spectroscopic analysis of the ferric uptake regulator" Molecular Microbiology, vol. 47 (pp. 903-915), 2003.

Postle et al. "Touch and go: tying TonB to transport" Molecular Microbiology, vol. 49 (pp. 869-882), 2003.

Ramsay et al. "Modified Spectrophotometer for Multi-Dimensional Circular Dichroism/Fluoresence Data Acquisition in Titration Experiments: Application to the pH and Guanidine-HCI Induced Unfolding of Apomyoglobin" Biophysical Journal, vol. 69 (pp. 701-707), Aug. 1998.

Reeves et al. "TonB Is Required for Intracellular Growth and Virulence of *Shigella dysenteriae* " Infection and Immunity, vol. 68, No. 11 (pp. 6329-6336), Nov. 2000.

Rose et al. "The Kinetic Mechanism of Heme Binding to Human Apohemoglobin" The Journal of Biological Chemistry, vol. 258, No. 7 (pp. 4298-4303), Apr. 10, 1983.

Sassaroli et al. "Specialized Functional Domains in Hemoglobin: Dimensions in Solution of the Apohemoglobin Dimer Labeled with Fluorescein Iodoacetamide" Biochemistry 23 (pp. 2487-2491), 1984.

Scott et al. "The Stabilities of Mammalian Apomyoglobins Vary over a 600-Fold Range and Can Be Enhanced by Comparative Mutagenesis" The Journal of Biological Chemistry, vol. 275, No. 35 (pp. 27129-27136), Sep. 1, 2000.

Seliger et al. "The two TonB systems of *Vibrio cholerae*: redundant and specific functions" Molecular Microbiology, vol. 39 (pp. 801-812), 2001.

Shaeffer et al. "Dimer-Monomer Dissociation of Human Hemoglobin A" The Journal of Biological Chemistry, vol. 259, No. 23 (pp. 14544-14547), Dec. 10, 1984.

Shen et al. "Production of human normal adult and fetal hemoglobins in *Escherichia coli*" Protein Engineering, vol. 10 (1 page), 1997.

Smith, "The Effects of Amino Acid Substitution on Apomyoglobin Stability, Folding Intermediates, and Holoprotein Expression", Ph.D. Dissertation, Biochemistry & Cell Biology, Rice University Houston Texas, 2003.

Snyder "Respiratory Adaptions in Diving Mammals" Respiration Physiology 54 (pp. 296-294), 1983.

Springer et al. "High-level expression of sperm whale myoglobin in *Escherichia coli*" Proc. Natl. Acad. Sci., Vol. 84 (pp. 8961-8965), Dec. 1987.

Stojiljkovic et al. "Hemin uptake system of *Yersinia enterocolitica*: similarities with other TonB-dependent systems in Gram-negative bacteria" The EMBO Journal, vol. 11, No. 12 (pp. 4359-4367), 1992.

Stojiljkovic et al. "Processing of Heme and Heme-Containing Proteins by Bacteria" DNA and Cell Biology, vol. 21, No. 4 (pp. 281-295), 2002.

Tang et al. "Disruption of the Heme Iron-Proximal Histidine Bond Requires Unfolding of Deoxymyoglobin" Biochemistry 37 (pp. 7047-7056), Feb. 26, 1998.

Thompson et al. "Molecular Characterization of the Hemin Uptake Locus (*hmu*) from *Yersinia pestis* and Analysis of *hmu* Mutants for Hemin and Hemoprotein Utilization" Infection and Immunity, vol. 67, No. 8 (pp. 3879-3892), Aug. 1999.

Torres et al. "Haem iron-transport system in enterohaemorrhagic *Escherichia coli* O157:H7" Molecular Microbiology, vol. 23 (pp. 825-833), 1997.

Varadarajan et al. "Cloning, expression in *Excherichia coli*, and reconstitution of human myoglobin" Proc. Natl. Acad. Sci., vol. 82 (pp. 5681-5684), Sep. 1985.

Vasudevan et al. "Ordered Heme Binding Ensures the Assembly of Fully Functional Hemoglobin: A Hypothesis" Current Protein and Peptide Science 3 (pp. 461-466), 2002.

Vasudevan et al. "Spectral Demonstration of Semihemoglobin Formation during CN-Hemin Incorporation into Human Apohemoglobins" The Journal of Biological Chemistry, vol. 272, No. 1 (pp. 517-524), Jan. 3, 1997.

Vasudevan et al. "Wavelength-Dependent Spectral Changes Accompany CN-Hemin Binding to Human Apohemoglobin" Journal of Protein Chemistry, vol, 19, No. 7 (pp. 583-590), 2000.

Varnado et al. "System for the expression of recombinant hemoproteins in *Escherichia coli*" Protein Expression and Purification 35 (pp. 76-83), 2004.

Villaloboz et al. "0-083. Using *Escherichia coli* Containing the *Plesiomonas shigelloides* Heme Transport System to Increase the Production of Myoglobin" Abstracts of the General Meeting of the American Society for Microbiology, vol. 103, Abstr 0-083; Issn: 1060-2011 (pg. 482), 2003.

Volkmar et al. "Iron transport and signaling in *Escherichia coli*" FEBS Letters 529 (pp. 78-85), 2002.

Waks et al. "Influence of Prosthetic Groups on Protein Folding and Subunit Assembly" The Journal of Biological Chemistry, vol. 248, No. 18 (pp. 6462-6470), Sep. 25, 1973.

Wiedermann et al. "Acceleration of Tetramer Formation by the Binding of Inositol Hexaphosphate to Hemoglobin Dimers" The Journal of Biological Chemistry, vol. 250, No. 13 (pp. 5273-5275), Jul. 10, 1975.

Yamaguchi et al. "Surface and Interface β-Chain Residues Synergistically Affect Hemoglobin Assembly" Biochemical and Biophysical Research Communications 270 (pp. 683-687), Mar. 7, 2000.

Zapol et al. "Regional blood flow during simulated diving in the conscious Weddell seal" J Applied Physiol, the American Physiological Society 47 (pp. 968-973), 1979.

Supplementary European Search Report for Application No. EP 05796424.9 dated Jan. 20, 2009 (6 pages).

* cited by examiner

ENHANCING RECOMBINANT HEMOGLOBIN PRODUCTION BY CO-EXPRESSION WITH ALPHA HEMOGLOBIN STABILIZING PROTEIN

RELATED APPLICATION

This application is a continuation of International Patent Application No. PCT/US2005/033028, filed on Sep. 15, 2005, which claims priority to U.S. Provisional Patent Application No. 60/610,108, filed on Sep. 15, 2004, U.S. Provisional Patent Application No. 60/610,109, filed on Sep. 15, 2004, and U.S. Provisional Patent Application No. 60/610,110, filed on Sep. 15, 2004, the full disclosures of which are incorporated herein by reference.

TECHNICAL FIELD

The present disclosure relates to compositions and/or methods of producing compositions that include a form of hemoglobin.

BACKGROUND

Hemoglobin (Hb) is responsible for carrying and delivering oxygen to tissues and organs in animals and has been used in development of an effective and safe oxygen carrier as an alternative to blood transfusion. Hb can be obtained easily in large quantities from bovine sources, or can be produced transgenically, so the raw material is not limiting. Such forms of Hb, however, may have numerous serious side effects when transfused into a human patient. For example, raw Hb may cause vasoconstriction, abdominal pain, and acute kidney failure. In addition, products may cause elevation of blood pressure and other problems associated with interference with smooth muscle regulation.

Some of these effects may stem from the toxicity of Hb when it is outside of a red blood cell (erythrocyte). In addition, Hb outside of a red blood cell is rapidly broken down from its tetrameric form into dimers and monomers. These products may be taken up by the kidney and impair nephrological functions. Production of hemoglobin (Hb) may be limited by the stability of the globin chains (protein without the heme bound), particularly the α subunits which are generally less stable than the partner β subunits.

SUMMARY

Therefore, a need exists for oxygen delivery compositions that are safer, more clinically effective, and/or more economically produced. In addition, there is a need for compositions, systems, and methods for increasing the stability of hemoglobin (Hb) subunits (e.g., the α subunit). Improvements that lower production costs or decrease degradation products or otherwise provide a commercially applicable benefit are particularly needed, which may facilitate commercial production of Hb and/or provide additional benefits.

The present disclosure, according to some example embodiments, relates to methods of producing hemoglobin comprising contacting the hemoglobin with an α hemoglobin stabilizing protein (e.g., a wild-type form, a derivative thereof, and a mutant thereof; collectively "AHSP"). For example, a nucleic acid encoding hemoglobin and a nucleic acid encoding AHSP may be co-expressed in a cell. According to some embodiments, AHSP stabilization may be used to increase the production of intact hemoglobin in various systems, such as $E.\ coli$, other microorganism, or animal erythroid cells. In some embodiments, hemoglobin so-produced may be used as or in a blood substitute.

According to some embodiments, a hemoglobin subunit may be a wild-type or modified form of hemoglobin subunit from any species. For example, a wild-type or recombinant form of human hemoglobin may be used. In some specific example embodiments, human globin and human AHSP may be used. Both α and β globin and AHSP may all be expressed from transgenic nucleic acids in a single cell, such as an $E.\ coli$ cell, other microorganisms, such a yeast or other bacteria, or an animal erythroid cell, particularly a mammalian erythroid cell. For example, plasmid vectors may be used to achieve co-expression.

Additional example embodiments of the present disclosure include hemoglobin production cells, tissues, or animals in which AHSP is provided to stabilize a hemoglobin molecule, such as a hemoglobin. Other embodiments may relate to nucleic acids that encode AHSP and at least two different hemoglobin subunits for co-expression in the same cell to produce hemoglobin. Still other example embodiments relate to systems including cells, such as $E.\ coli$ cells, other microorganisms, or animal erythroid cells, in which a hemoglobin or another hemoglobin is stabilized by AHSP. These systems may also exhibit increased hemoglobin production and fewer degradation products when compared with similar systems lacking AHSP. Other example embodiments relate to methods of making the above cells and nucleic acids, as well as to methods of producing recombinant hemoglobin by stabilizing α hemoglobin with AHSP.

BRIEF DESCRIPTION OF THE DRAWINGS

The present disclosure may be better understood through reference to the following detailed description, taken in conjunction with the following figures in which.

DETAILED DESCRIPTION

The present disclosure, according to one example embodiment, relates to the use of AHSP to stabilize the α subunit of rHb. AHSP may be provided by any available means. For example, AHSP may be co-expressed with a hemoglobin gene in a cell. AHSP stabilization may be used to increase the production of intact rHb in various systems, such as $E.\ coli$, other microorganisms, such as yeast or other bacteria, or animal erythroid cells, particularly mammalian erythroid cells. This intact rHb may then be used as part of a blood substitute product.

In specific example embodiments, human globin and human AHSP may be used. Both α and β globin and AHSP may all be expressed from transgenic nucleic acids in a single cell, such as an $E.\ coli$ cell, other microorganisms, or an animal erythroid cell. For example, plasmid vectors may be used to achieve co-expression.

Without being limited to any particular mechanism of action or theory, in some example embodiments, AHSP may facilitate folding of the α subunits and in turn facilitate their reaction with β subunits to form assembled hemoglobin dimers and tetramers. These dimers and tetramers, in some embodiments, may be much more stable and/or may rapidly bind heme. In some example embodiments of the present disclosure, the AHSP surface that interacts with α globin may be modified to stabilize other globin subunits and also to catalyze the assembly of almost any hemoglobin in bacteria. For example, it may be modified to stabilize the β globin subunit.

Thus, some example embodiments of the present disclosure include rHb production cells, tissues, or animals, in which AHSP is provided to stabilize a hemoglobin molecule, such as α hemoglobin. Some example embodiments may relate to nucleic acids that encode AHSP and at least two different hemoglobin subunits for co-expression in the same cell to produce rHb. Some example embodiments relate to systems including microorganisms (e.g., E. coli) or animal erythroid cells, in which α hemoglobin or another hemoglobin is stabilized by AHSP. These systems may also exhibit increased rHb production and fewer degradation products when compared with similar systems lacking AHSP. Other embodiments relate to methods of making the above cells and nucleic acids as well as to methods of producing rHb by stabilizing α hemoglobin with AHSP.

Certain embodiments of the present disclosure may be used in conjunction with existing rHb technologies. For example, it may be used in connection with U.S. provisional patent Nos. 60/610,109 and 60/610,108, as well as U.S. Pat. Nos. 6,455,676; 6,204,009; 6,114,505; 6,022,849; and U.S. patent application publication No. 2003 0017537 (all incorporated by reference herein).

The following discussion relates to specific example embodiments of the disclosure.

Figure 1:
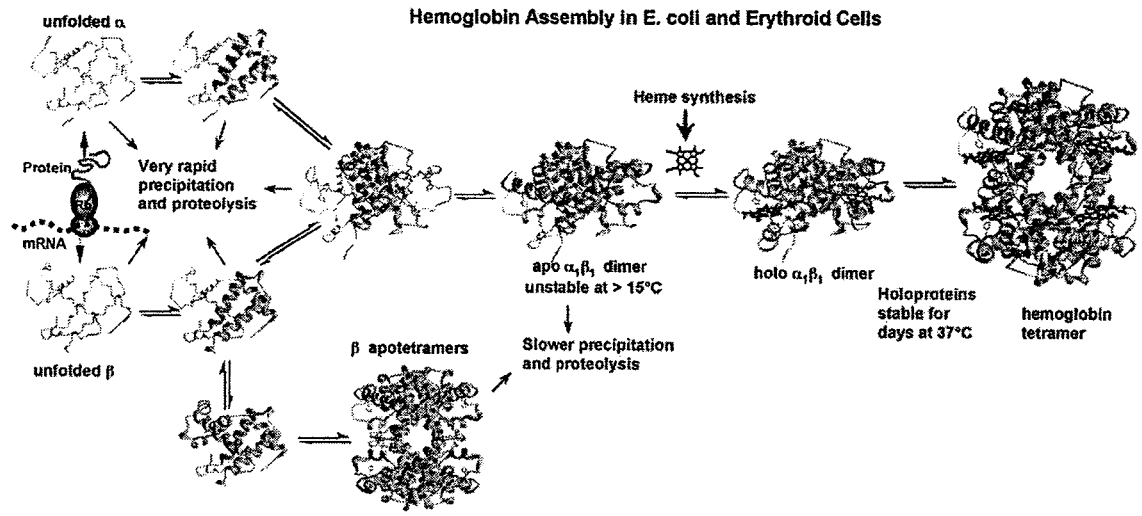
FIG. 1 illustrates a simple scheme for hemoglobin assembly in both $E.\ coli$, other microorganisms, and erythroid cells.

The assembly of hemoglobin in either bacterial or in animal erythroid cells is a complex process (FIG. 1) involving ribosomal synthesis of two different protein chains or subunits (α, 141 amino acids and β, 146 amino acids). The newly synthesized α and β subunits do not appear to have any well-formed structure in the absence of a partner, and first assemble to form an $\alpha_1\beta_1$ dimer, which itself is very unstable (apo $\alpha_1\beta_1$ dimer in FIG. 1, where the suffix apo means no heme is bound and the protein has no "red" color). Only after heme (iron containing red pigment) is bound is the protein stabilized and resistant to degradation and precipitation. Hemoglobin synthesis in bacteria is limited by the availability of heme, and as a result, newly formed α and β proteins that are unable to find heme tend to precipitate or be degraded by bacterial enzymes, particularly α subunits. AHSP may help stabilize the newly made α subunits until heme is available. The β subunits can stabilize themselves by self-associating to form relatively stable tetramers (see FIG. 1). However, in some cases further stabilization of the β subunits may be useful.

Alpha hemoglobin stabilizing protein (AHSP), an 102 amino acid protein, expression may be induced by GATA-1, an essential erythroid transcription factor (Kihm, A J. et al. (2002) Nature 417, 758-763). Expression of this protein may progressively increase during normal human erythropoiesis to levels of ~0.1 mM in pro-erythroblasts (dos Santos, C. O. et al. (2004) Exp Hematol 32, 157-162). AHSP may bind isolated holo-α subunits reversibly with an association equilibrium constant equal to $10\,\mu M^{-1}$. Holo-β chains may readily displace α subunits from AHSP to form intact hemoglobin (Kihm, A J. et al. (2002) Nature 417, 758-763; Santiveri, C. M. et al. (2004) J Biol Chem; Gell, D. et al. (2002) J Biol Chem 277, 40602-40609) because the equilibrium constant for the formation of holo-$\alpha_1\beta_1$ dimers is ~60,000 times greater than that for formation of the AHSP-α chain complex. Furthermore, it has been shown that "knocking out" the AHSP gene causes formation of α globin aggregates and Heinze bodies in red cells from normal mice, and exacerbates these processes in animals with β-thalassemia. Oxidation of bound α chains leads to slow formation of a stable hemichrome (Gell, D. et al. (2002) J Biol Chem 277, 40602-40609), and interaction of α apoglobin with AHSP induces partial folding of the hemoglobin subunit. Marden's group in Paris has recently confirmed Gell et al.'s observations and discovered that CO binding to α chain is altered by binding to AHSP (Baudin-Creuza, v. et al. (2004) J Biol Chem). Bycroft's group in Cambridge, U.K. has solved the NMR solution structure of AHSP (Santiveri, C. M. et al. (2004) J Biol Chem). The protein forms a remarkably stable 3-helix bundle with a surface that appears to mimic the β subunit portion of the $\alpha_1\beta_1$ interface. The residues forming this surface on AHSP were determined directly in NMR experiments with the α subunit-AHSP complex.

Figure 2:
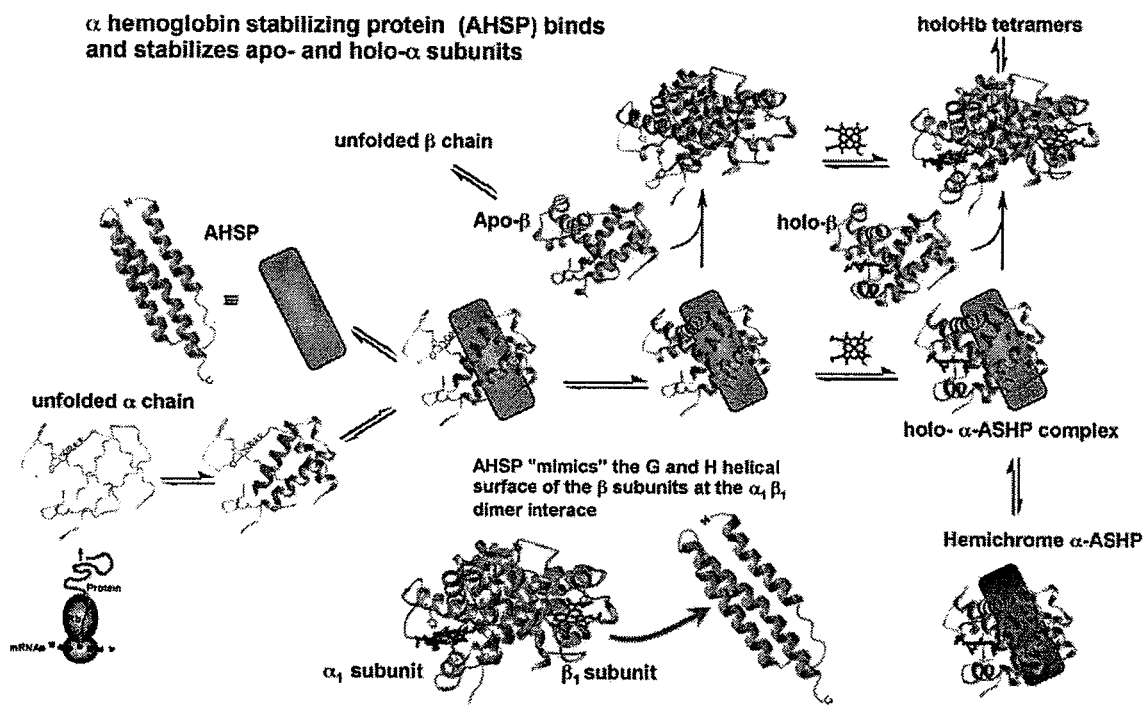
FIG. 2 illustrates possible functions of AHSP in facilitating α chain folding and hemoglobin formation.

Possible functions of AHSP during hemoglobin assembly are shown in FIG. 2, which is based on the molecular genetic, functional, and structural work of Weiss, Mackay, Bycroft, and coworkers (Kihm, A J. et al. (2002) Nature 417, 758-763; Santiveri, C. M. et al. (2004) J Biol Chem; and Gell, D. et al. (2002) J Biol Chem 277, 40602-40609). The three-helical bundle structure was taken from Santiveri et al. (PDB 1w09, (Santiveri, C. M. et al. (2004) J Biol Chem)). Weiss and Mackay have speculated that the primary purpose of AHSP is to prevent toxic effects from excess α globin synthesis by binding the α subunits and forming a hemichrome that prevents hemin loss, formation of radical oxygen species, and precipitation (Kihm, A J. et al. (2002) Nature 417, 758-763; Kong, Y. et al. (2004) J Clin. Invest.). AHSP may also act as a hemoglobin chaperone to facilitate the initial folding of α subunits and allow more efficient and rapid formation of either apo- or heme-containing $\alpha_1\beta_1$ dimers (Kihm, A J. et al. (2002) Nature 417, 758-763; Luzzatto, L. et al. (2002) Nature 417, 703-705). Newly formed β subunits assemble into apo- or heme-containing $\beta_4$ tetramers (McGovern, P. et al. (1976) J Biol Chem 251, 7871-7879; Ip, S. H. et al. (1976) Biochemistry 15, 654-660; O'Malley, S. M. et al. (1994) J Protein Chem 13, 585-590) and appear to act as self-chaperones. AHSP, when used in accordance with example embodiments of the present disclosure, may greatly facilitate hemoglobin formation in E. coli (and other microorganisms) and increase production to levels that make recombinant hemoglobin a feasible commercial starting material for blood substitutes.

The chaperon activity of AHSP may be tested by co-expressing it with rHb in E. coli (and other microorganisms) and measuring changes in holohemoglobin expression. The effects of variant AHSP proteins, particularly those with different interface binding, may be tested in a similar manner.

The system for co-expression AHSP with α (and β) hemoglobin in E. coli (or other microorganisms) may be optimized by: (i) subcloning various forms of the AHSP gene; (ii) inserting the AHSP gene into high and low copy vectors to regulate the level of AHSP chaperone activity; (iii) changing the AHSP promoter to an alternative inducer system to allow pre-expression of the AHSP gene; and (iv) constructing a low copy number plasmid containing both AHSP and other helper genes under control of an alternative promoter that could be incorporated into the bacterial chromosome. When an appropriate system is located, the relevant set of genes may be incorporated into the E. coli chromosome (or that of other microorganisms) to create a modular heme protein expression strain. Similar steps may also be followed to optimize systems in other cells, tissues, or organisms, such as animal erythroid cells.

Figure 3:
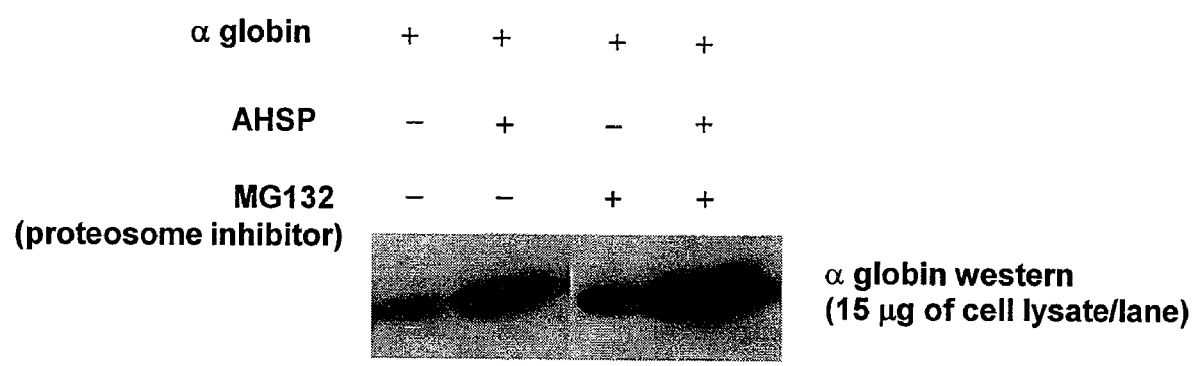
FIG. 3 illustrates enhanced expression of α globin in COS cells in the presence and absence of a proteosome inhibitor.

Full-length human AHSP cDNA (GenBank AF147435) has been cloned into the glutathione S-transferase (GST) fusion vector pGEX-2T (Amersham Biosciences). This plasmid may be used in co-expression. The fusion protein may be expressed in *E. coli* BL21 cells and purified by affinity chromatography as described by Gell et al. (Gell, D. et al. (2002) *J Biol Chem* 277, 40602-40609).

rHb pSGE1702 (pHb0.0) and pGEX-2T (AHSP) vectors (Baxter) may be used to co-transform *E.coli* and the HbCO derivative spectrum assay may be used to look for enhanced holo-Hb production. Mackay and Gell have observed that α chains bind equally well to the GST fusion protein and cleaved AHSP, and this observation has been confirmed by Marden and co-workers (Baudin-Creuza, v. et al. (2004) *J Biol Chem*). The pHb0.0 and pGEX-2T vectors may be maintained in *E. coli* by growth on tetracycline and ampicillin, and both expression systems are induced by IPTG. And AHSP has been shown to promote α chain synthesis in COS cells (FIG. 3). Methods similar to those used by Baudin-Creuza et al. (Baudin-Creuza, v. et al. (2004) *J Biol Chem*) may also be employed.

The pGET-2T version of the His-tag AHSP expression vector may be used for sub-cloning the AHSP gene (without the His-tag) into the PTARA T7 expression vector(Wycuff, D. R. and Matthews, K. S. Generation of an AraC-araBAD Promoter-Regulated T7 Expression System (2000) *Anal. Biochem.* 277, 67-73). AHSP also may be subcloned into pBAD33 under control of the AraC protein/araBAD promoter system (Wycuff, D. R. et al. (2000) *Anal. Biochem.* 277, 67-73). Thus, AHSP expression may be induced with arabinose and rHb with IPTG. In some example embodiments, both AHSP and a heme transport gene, for example, a hug gene from *P. shigelloides*, may be subcloned into pBAD33.

Systems discussed above may be further optimized to balance the production of AHSP and this hemoglobin stabilization with the other metabolic needs of the cell, tissue, or animal, and the metabolic needs for hemoglobin production.

Although the present disclosure and its advantages have been described in detail, it should be understood that various changes, substitutions and alterations can be made herein without departing from the spirit and scope of the disclosure as defined by the following claims.

What is claimed is:

1. A method of producing a recombinant hemoglobin α subunit comprising co-expressing a nucleic acid encoding the recombinant hemoglobin α subunit, a nucleic acid encoding a recombinant α hemoglobin stabilizing protein, and a recombinant heme transport gene product in an *Escherichia coli* or a non-*Escherichia coli* microorganism cell.

2. A method according to claim 1, wherein the recombinant hemoglobin α subunit is a human recombinant hemoglobin α subunit and the recombinant α hemoglobin stabilizing protein is a human recombinant α hemoglobin stabilizing protein.

3. A method according to claim 1, wherein the nucleic acid encoding the α hemoglobin stabilizing protein is located in a plasmid.

4. A method according to claim 1, wherein the nucleic acid encoding the recombinant hemoglobin α subunit is located in a plasmid.

5. A method according to claim 1, wherein the nucleic acid encoding the heme transport gene product is located in a plasmid.

6. A method according to claim 1, wherein the nucleic acid encoding the recombinant α hemoglobin stabilizing protein, the recombinant hemoglobin α subunit, and the recombinant heme transport gene product are located in a single plasmid.

7. A recombinant hemoglobin α subunit production cell comprising:
    a nucleic acid encoding a recombinant hemoglobin α subunit;
    a nucleic acid encoding a recombinant α hemoglobin stabilizing protein; and
    a nucleic acid encoding a recombinant heme transport gene,
    wherein the recombinant α hemoglobin stabilizing protein stabilizes the recombinant hemoglobin α subunit; and
    wherein the cell is a *Escherichia coli* or a non-*Escherichia coli* microorganism cell.

8. A cell according to claim 7, wherein the recombinant hemoglobin α subunit is a human recombinant hemoglobin α subunit and the recombinant α hemoglobin stabilizing protein is a human recombinant α hemoglobin stabilizing protein.

9. A cell according to claim 7 further comprising a plasmid comprising the nucleic acid encoding the recombinant α hemoglobin stabilizing protein.

10. A cell according to claim 7, further comprising a plasmid comprising the nucleic acid encoding the recombinant hemoglobin α subunit.

11. A cell according to claim 7, further comprising a plasmid comprising the nucleic acid encoding the recombinant heme transport gene product.

12. A cell according to claim 7, further comprising a single plasmid comprising the nucleic acid encoding the recombinant α hemoglobin stabilizing protein, the recombinant hemoglobin α subunit, and the recombinant heme transport protein.

13. A system for recombinant hemoglobin subunit production comprising:
    an *Escherichia coli* or non-*Escherichia coli* microorganism production cell;
    a nucleic acid encoding a recombinant hemoglobin α subunit;
    a nucleic acid encoding an α hemoglobin stabilizing protein; and
    a nucleic acid encoding a recombinant heme transport gene product,
    wherein the nucleic acid encoding the recombinant hemoglobin α subunit and the nucleic acid encoding the recombinant α hemoglobin stabilizing protein are co-expressed and the recombinant α hemoglobin stabilizing protein stabilizes at least one recombinant hemoglobin α subunit.

14. A system according to claim 13, wherein the recombinant hemoglobin α subunit is a human recombinant hemoglobin α subunit and the recombinant α hemoglobin stabilizing protein is a human recombinant α hemoglobin stabilizing protein.

15. A system according to claim 13, further comprising a plasmid comprising the nucleic acid encoding the recombinant α hemoglobin stabilizing protein.

16. A system according to claim 13, further comprising a plasmid comprising the nucleic acid encoding the recombinant hemoglobin α subunit.

17. A system according to claim 13, further comprising a plasmid comprising the nucleic acid encoding the recombinant heme transport gene product.

18. A system according to claim 13, further comprising a single plasmid comprising the nucleic acid encoding the recombinant hemoglobin α subunit, the nucleic acid encoding the recombinant α hemoglobin stabilizing protein, and the nucleic acid encoding the recombinant heme transport gene product.

19. The system according to claim 13, further comprising a nucleic acid encoding a recombinant hemoglobin β subunit.

20. A system according to claim 13, wherein the system produces recombinant hemoglobin that may be used as part of a blood substitute product.

* * * * *